(12) United States Patent
Schloss et al.

(10) Patent No.: US 8,771,746 B2
(45) Date of Patent: Jul. 8, 2014

(54) COLLOIDAL SUSPENSIONS COMPRISING A THERAPEUTIC AGENT AND SQUALENE

(75) Inventors: John Vinton Schloss, Portland, ME (US); Thomas Jay Lobl, Valencia, CA (US)

(73) Assignee: Otonomy, Inc., San Diego, CA (US)

( * ) Notice: Subject to any disclaimer, the term of this patent is extended or adjusted under 35 U.S.C. 154(b) by 535 days.

(21) Appl. No.: 13/146,618

(22) PCT Filed: Jun. 18, 2009

(86) PCT No.: PCT/US2009/047764
§ 371 (c)(1),
(2), (4) Date: Apr. 27, 2012

(87) PCT Pub. No.: WO2009/155401
PCT Pub. Date: Dec. 23, 2009

(65) Prior Publication Data
US 2012/0208851 A1 Aug. 16, 2012

Related U.S. Application Data

(60) Provisional application No. 61/074,135, filed on Jun. 19, 2008.

(51) Int. Cl.
*A61K 9/50* (2006.01)

(52) U.S. Cl.
USPC .......................................................... 424/501

(58) Field of Classification Search
None
See application file for complete search history.

(56) References Cited

U.S. PATENT DOCUMENTS

2002/0039594 A1* 4/2002 Unger .......................... 424/426
2006/0205789 A1* 9/2006 Lobl et al. .................... 514/326

* cited by examiner

*Primary Examiner* — Carlos Azpuru
(74) *Attorney, Agent, or Firm* — Banner & Witcoff, Ltd.

(57) ABSTRACT

Colloidal suspensions comprising a therapeutic agent and squalene. Squalene binds to certain compounds, such as gacyclidine, much more tightly than other drug carriers, such as polylactic glycolic acid. Including squalene in the particulate phase sequesters the therapeutic agent and provides superior stability at room or body temperature.

3 Claims, 3 Drawing Sheets

COLLOIDAL SUSPENSIONS COMPRISING A THERAPEUTIC AGENT AND SQUALENE

FIELD OF THE INVENTION

The invention relates to formulations of gacyclidine and other pharmaceutical compounds with improved stability.

BACKGROUND OF THE INVENTION

Gacyclidine is a promising neuroprotective drug with potential for tinnitus suppression. However, in solution gacyclidine is unstable at room or body temperature and decomposes at a rate that is incompatible with long-term drug therapy. There is a need for stable formulations of gacyclidine and for other therapeutic compounds of limited stability.

DETAILED DESCRIPTION OF THE INVENTION

Figure 1:
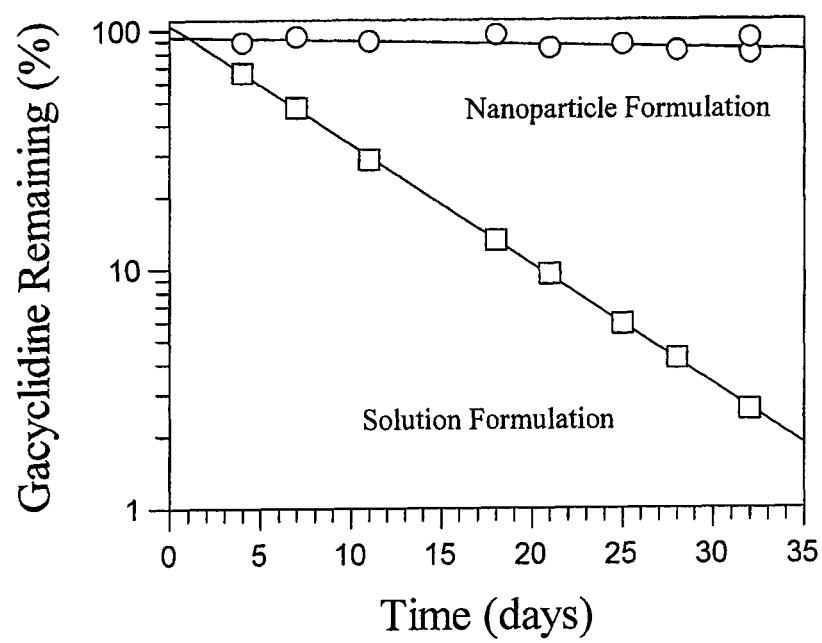
FIG. 1 compares the amount of gacyclidine over time in samples of a gacyclidine solution and in samples of a gacyclidine-squalene nanoparticle formulation.

The invention involves a method for improving the aqueous stability of gacyclidine and other hydrophobic compounds by co-formulation with squalene.

The basic form of gacyclidine is water insoluble, but it is much more stable than the water-soluble, but unstable acid form. Due to the low affinity of PLGA for the basic form of gacyclidine, initial attempts to use nanoparticles containing polylactic-glycolic acid (PLGA) polymers to improve gacyclidine stability were not successful. Unexpectedly, it was found that most excipients did not have sufficient affinity for the basic form of gacyclidine to provide a substantial increase in the stability of aqueous gacyclidine formulations. Equally surprising was the observation that squalene, a molecule with similar solubility to PLGA, had the ability to sequester the basic form of gacyclidine, thereby reducing its concentration in the aqueous phase of squalene-water emulsions and improving gacyclidine stability dramatically.

Gacyclidine has improved thermal stability in stable squalene-water emulsions. It can pass through antibacterial membrane filters and exhibits reduced losses at equilibrium in the presence of various polymers relative to solution formulations of the acid form of gacyclidine. Squalene-water emulsions are a superior vehicle for gacyclidine formulations to be implanted at body temperature (37° C.) or long-term storage at room temperature. Squalene-containing formulations can also be subjected to sterile filtration with minimal loss of gacyclidine from the formulation. Including squalene in the formulation also reduces losses of gacyclidine that may be encountered by binding of the drug to catheters or other components of delivery devices.

The specific examples below describe gacyclidine formulations. However, squalene formulations as described herein are useful for stabilizing a variety of hydrophobic compounds with are essentially insoluble in their free base form, including ketamine and other phencyclidine analogs, and other compounds, including prostaglandins e.g., misoprostal, latanoprost), steroids (e.g., methyl prednisolone, dexamethasone, triamcinolone acetonide), ebselen, anxiolytics, antidepressants, selective serotonin reuptake inhibitors (SSRI), calcium channel blockers, sodium channel blockers, antimigraine agents (e.g., flunarizine), muscle relaxants, hypnotics, and anti-convulsants, including anti-epileptic agents. Examples of such compounds are provided below.

Anticonvulsants

Anticonvulsants include barbiturates (e.g., mephobarbital and sodium pentobarbital); benzodiazepines, such as alprazolam (XANAX®), lorazepam, clonazepam, clorazepate dipotassium, and diazepam (VALIUM®); GABA analogs, such as tiagabine, gabapentin (an α2δ antagonist, NEURONTIN®), and β-hydroxypropionic acid; hydantoins, such as 5,5-diphenyl-2,4-imidazolidinedione (phenyloin, DILANTIN®) and fosphenytoin sodium; phenyltriazines, such as lamotrigine; succinimides, such as methsuximide and ethosuximide; 5H-dibenzazepine-5-carboxamide (carbamazepine); oxcarbazepine; divalproex sodium; felbamate, levetiracetam, primidone; zonisamide; topiramate; and sodium valproate.

NMDA Receptor Antagonists

There are many known inhibitors of NMDA receptors, which fall into five general classes. Each of the compounds described below includes within its scope active metabolites, analogs, derivatives, compounds made in a structure analog series (SAR), and geometric or optical isomers which have similar therapeutic actions.

Competitors for the NMDA Receptor Glutamate Binding Site

Antagonists which compete for the NMDA receptor's glutamate-binding site include LY 274614 (decahydro-6-(phosphonomethyl)-3-isoquinolinecarboxylic acid), LY 235959[(3S,4aR,6S,8aR)-decahydro-6-(phosphonomethyl)-3-isoquinolinecarboxylic acid], LY 233053 ((2R,4S)-rel-4-(1H-tetrazol-5-yl-methyl)-2-piperidine carboxylic acid), NPC 12626 (α-amino-2-(2-phosphonoethyl)-cyclohexanepropanoic acid), reduced and oxidized glutathione, carbamathione, AP-5 (5-phosphono-norvaline), CPP (4-(3-phosphonopropyl)-2-piperazine-carboxylic acid), CGS-19755 (seifotel, cis-4(phono-methyl)-2-piperidine-carboxylic acid), CGP-37849 ((3E)-2-amino-4-methyl-5-phosphono-3-pentenoic acid), CGP 39551 ((3E)-2-amino-4-methyl-5-phosphono-3-pentenoic acid, 1-ethyl ester), SDZ 220-581[(αS)-α-amino-2'-chloro-5-(phosphonomethyl)-[1, 1'-biphenyl]-3-propanoic acid], and S-nitrosoglutathione. See Gordon et al., 2001; Ginski and Witkin, 1994; Calabresi et al., 2003; Hermann et al., 2000; Kopke et al., 2002; Ikonomidou and Turski, 2002; Danysz and Parsons, 1998.

Non-Competitive Inhibitors which Act at the NMDA Receptor-Linked Ion Channel

Antagonists which are noncompetitive or uncompetitive and act at the receptor-linked ion channel include amantadine, aptiganel (CERESTAT®, CNS 1102), caroverine, dextrorphan, dextromethorphan, fullerenes, ibogaine, ketamine, lidocaine, memantine, dizocilpine (MK-801), neramexane (MRZ 2/579, 1,3,3,5,5-pentamethyl-cyclohexanamine), NPS 1506 (delucemine, 3-fluoro-γ-(3-fluorophenyl)-N-methylbenzenepropanamine hydrochloride), phencyclidine, tiletamine and remacemide. See Palmer, 2001; Hewitt, 2000; Parsons et al., 1995; Seidman and Van De Water, 2003; Danysz et al., 1994; Ikonomidou and Turski, 2002; Feldblum et al., 2000; Kohl and Dannhardt, 2001; Mueller et al., 1999; Sugimoto et al., 2003; Popik et al., 1994; Hesselink et al., 1999.

Antagonists which Act at or Near the NMDA Receptor's Polyamine-Binding Site

Antagonists which are thought to act at or near the NMDA receptor's polyamine-binding site include acamprosate, arcaine, conantokin-G, eliprodil (SL 82-0715), haloperidol, ifenprodil, traxoprodil (CP-101,606), and Ro 25-6981 [(±)-(R,S)-α-(4-hydroxyphenyl)-β-methyl-4-(phenylmethyl)-1-piperidine propanol]. See Mayer et al., 2002; Kohl and Dannhardt, 2001; Ikonomidou and Turski, 2002; Lynch et al., 2001; Gallagher et al., 1996; Zhou et al., 1996; 1999; Lynch and Gallagher, 1996; Nankai et al., 1995.

Antagonists which Act at the NMDA Receptor's Glycine-Binding Site

Antagonists which are thought to act at the receptor's glycine-binding site include aminocyclopropanecarboxylic acid (ACPC), 7-chlorokynurenic acid, D-cycloserine, gavestinel (GV-150526), GV-196771A (4,6-dichloro-3-[(E)-(2-oxo-1-phenyl-3-pyrrolidinylidene)methyl]-1H-indole-2-carboxylic acid monosodium salt), licostinel (ACEA 1021), MRZ-2/576 (8-chloro-2,3-dihydropyridazino[4,5-b]quinoline-1,4-dione 5-oxide 2-hydroxy-N,N,N-trimethyl-ethanaminium salt), L-701,324 (7-chloro-4-hydroxy-3-(3-phenoxyphenyl)-2 (1H)-quinolinone), HA-966 (3-amino-1-hydroxy-2-pyrrolidinone), and ZD-9379 (7-chloro-4-hydroxy-2-(4-methoxy-2-methylphenyl)-1,2,5,10-tetra-hydropyridanizo[4,5-b] quinoline-1,10-dione, sodium salt). Peterson et al., 2004; Danysz and Parsons, 2002; Ginski and Witkin, 1994; Petty et al., 2004; Danysz and Parsons, 1998.

Antagonists which Act at the NMDA Receptor's Allosteric Redox Modulatory Site

Antagonists which are thought to act at the allosteric redox modulatory site include oxidized and reduced glutathione, S-nitrosoglutathione, sodium nitroprusside, ebselen, and disulfuram (through the action of its metabolites DETC-MeSO and carbamathione). See Hermann et al., 2000; Ogita et al., 1998; Herin et al., 2001, Ningaraj et al., 2001; Kopke et al., 2002.

Some NMDA receptor antagonists, notably glutathione and its analogs (S-nitrosoglutathione and carbamathione), can interact with more than one site on the receptor.

CNQX (1,2,3,4-tetrahydro-7-nitro-2,3-dioxo-6-quinoxalinecarbonitrile) and DNQX (1,4-dihydro-6,7-dinitro-2,3-quinoxalinedione) bind to non-NMDA glutamate receptors. These and other antagonists or agonists for glutamate receptors can be used in the methods of the invention.

It is preferable that the NMDA receptor antagonists, like those disclosed herein, inhibit NMDA receptors without inhibiting AMPA receptors. The reason for this is that inhibition of AMPA receptors is thought to result in impairment of hearing. By contrast, selective inhibition of NMDA receptors is expected to prevent initiation of apoptosis, programmed cell death, of the neuron. Unlike AMPA receptors, which are activated by glutamate alone, NMDA receptors require a co-agonist in addition to glutamate. The physiologic co-agonist for NMDA receptors is glycine or D-serine. NMDA receptors but not AMPA receptors also bind reduced glutathione, oxidized glutathione, and S-nitrosoglutathione. Glutathione, γ-glutamyl-cysteinyl-glycine, is thought to bridge between the glutamate and glycine binding sites of NMDA receptors, binding concurrently at both sites. Activation of NMDA receptors leads to entry of calcium ions into the neuron through the linked ion channel and initiation of $Ca^{2+}$-induced apoptosis. Intracellular calcium activates the NMDA receptor-associated neuronal form of nitric oxide synthase (nNOS), calpain, caspases and other systems linked to oxidative cell damage. Inhibition of NMDA receptors should prevent death of the neuron.

Subtype-Specific NMDA Receptor Antagonists

A variety of subtype-specific NMDA receptor agonists are known and can be used in methods of the invention. For example, some NMDA receptor antagonists, such as arcaine, argiotoxin636, Co 101244 (PD 174494, Ro 63-1908, 1-[2-(4-hydroxyphenoxy)ethyl]-4-[(4-methylphenyl)methyl-4-piperidinol], despiramine, dextromethorphan, dextrorphan, eliprodil, haloperidol, ifenprodil, memantine, philanthotoxin343, Ro-25-6981 ([(±)-(R*, S*)-α-(4-hydroxyphenyl)-β-methyl-4-(phenylmethyl)-1-piperidine propanol]), traxoprodil (CP-101,606), Ro 04-5595 (1-[2-(4-chlorophenyl)ethyl]-1,2,3,4-tetrahydro-6-methoxy-2-methyl-7-isoquinolinol), CPP [4-(3-phosphonopropyl)-2-piperazinecarboxylic acid], conantokin G, spermine, and spermidine have moderate or high selectivity for the NR2B (NR1A/2B) subtype of the receptor. NVP-AAM077 [[[(1S)-1-(4-bromophenyl)ethyl]amino](1,2,3,4-tetrahydro-2,3-dioxo-5-quinoxalinyl)methyl]-phosphonic acid] is an NR2A subtype-specific antagonist. See Nankai et al, 1995; Gallagher et al., 1996; Lynch and Gallagher, 1996; Lynch et al, 2001; Zhou et al., 1996; Zhou et al., 1999; Kohl and Dannhardt, 2001, Danysz and Parsons, 2002.

Antagonists such as 1-(phenanthrene-2-carbonyl) piperazine-2,3-dicarboxylic acid (Feng et al., Br J Pharmacol 141, 508-16, 2004), which has high selectivity for the NR2D and 2C subtypes of the receptor, are particularly useful.

Useful Therapeutics Other than NMDA Receptor Antagonists

Other useful therapeutic agents which can be formulated and administered according to the invention include nortriptyline, amytriptyline, fluoxetine (PROZAC®), paroxetine HCl (PAXIL®), trimipramine, oxcarbazepine (TRILEPTAL®), eperisone, misoprostol (a prostaglandin $E_1$ analog), latanoprost (a prostaglandin $F_2α$ analog) melatonin, and steroids (e.g., pregnenolone, triamcinolone acetonide, methylprednisolone, and other anti-inflammatory steroids).

Stable Particulate Formulations

Stable particulate formulations containing a mixture of squalene and gacyclidine (or other therapeutic agents as described above) can be prepared as either squalene-water emulsions or where squalene is adsorbed to nanoparticles or microparticles made of other materials. Either type of formulation can be used to treat or prevent various neurological disorders, such as age-related-noise- or drug-induced hearing loss; tinnitus; damage to hearing caused by the physical trauma of cochlear implant insertion; damage to hearing cause by blast or other types of physical trauma; physical or chemical trauma to the eye, vertigo or Meniere's Disease-related-, central nervous system (including the inferior colliculus and auditory cortex), or peripheral nerves; and any neurological damage mediated by activation of NMDA receptors.

Emulsions

Stable squalene-water emulsions can easily be prepared by mixing squalene with water in a range of from 0.1 to 50 volume percent (e.g., 0.1, 0.2, 0.25, 0.3, 0.5, 0.75, 1, 2, 5, 7, 10, 15, 20, 25, 30, 35, 40, 45, or 50%) and adding one or more amphipathic excipients to this mixture at 0.1 to 20 volume or weight percent relative to squalene (e.g., 0.1, 0.2, 0.25, 0.3, 0.5, 0.75, 1, 2, 5, 7, 10, 15, 20%). Any amphipathic excipient or combination of excipients which will coat the surface of squalene particles and thereby form a thermodynamically stable emulsion can be used. Examples of amphipathic excipients include, but are not limited to fatty acids and aqueous soluble lipids (e.g., cholic acid, chenic acid, deoxycholic acid, cardiolipin, cholylglycine, chenylglycine, deoxycholylglycine, cholyltaurine, chenyltaurine, deoxycholyltaurine); sulfatides (galactocerebrosides with a sulfate ester on the 3' position of the sugar); gangliosides; N-acetyl-D-neuraminic acid; phosphatidylinositol; surfactants such as polyoxyethylene esters of 12-hydroxystearic acid (e.g., SOLUTOL® HS 15), polysorbates, such as polysorbate 20, polysorbate 60, and polysorbate 80 (e.g., TWEEN 80®), d-alpha tocopheryl polyethylene glycol 1000 succinate (TPGS), ethylene glycol monostearate, glycerol stearate, glycerol mono-/di-caprylate/caprate, glyceryl behenate, glyceryl monooleate, glyceryl monostearate, glyceryl palmitostearate, lecithin, poloxamer 188, polyethylene glycols, polyglyceryl oleate, polyoxyl 40 stearate, polyoxyethylene sorbitan fatty acid esters, polyoxyethylene stearates, propylene glycol laurate, sodium lauryl sulfate, sodium stearyl fumarate, sorbitan esters (sorbitan fatty acid esters, e.g., sorbitan trioleate), sucrose octaacetate, stearic acid, and other pharmaceutically acceptable excipients useful for emulsifying water-insoluble compounds. See US 2006/0205789.

Gacyclidine or other therapeutic agents can be added to the formulation in the desired amount, up to their limit of solubility in the squalene phase. For gacyclidine, this is 1 gram of gacyclidine for every 9 milliliters of squalene, and the solubility of ketamine is similar.

Nanoparticles

The term "nanoparticle" refers to particles generally having a size of 200 nanometers (nm) or less, exclusive of temporary aggregation of such particles that might occur at high particle concentrations. Because of their size, Brownian motion will keep nanoparticles suspended in a fluid medium for a very long (or even indefinite) amount of time. Nanoparticles with diameters less than 200 nanometers will also be able to pass through antibacterial filters. If the nanoparticles are made of materials that lack a high affinity for gacyclidine or other therapeutic agents as disclosed herein, such as polylactic glycolic acid (PLGA, see EXAMPLE 1), then including squalene as part of the nanoparticle composition by admixture or adsorption, can increase the affinity of the nanoparticle for gacyclidine or other agent and thereby improve its stability.

Various methods, in addition to emulsion, can be employed to fabricate nanoparticles of suitable size. These methods include, but are not limited to, vaporization methods (e.g., free jet expansion, laser vaporization, spark erosion, electro explosion and chemical vapor deposition), physical methods involving mechanical attrition (e.g., the pearlmilling technology developed by Elan Nanosystems of Dublin, Ireland), and interfacial deposition following solvent displacement. The solvent displacement method for forming nanoparticles can involve rapid mixing, such as mixing two streams containing water miscible and water-insoluble components with a T-mixer, ball mixer, or Wiskind mixer.

The amount of squalene included in a nanoparticle composition can be between 1 to 50% by weight of the nanoparticle (e.g., 1-10%, 5-15%, 10-20%, 15-25%, 20-30%, 25-35%, 25-40%, 25-50%, 35-45%, or 1, 5, 10, 15, 20, 25, 30, 35, 40, 45, or 50%). The amount of drug included in the nanoparticle will be limited by the amount of squalene present. For gacyclidine, this is less than a weight to volume ratio of 1 gram of gacyclidine for every 9 milliliters of squalene (e.g., 1, 0.9, 0.8, 07, 0.6, 0.5, 0.4, 0.3, 0.2, 0.1 gram of gacyclidine for every 9 ml of squalene).

Stability Measurements

To compare the relative stability of particulate formulations (emulsions or other nanoparticles) containing squalene with solution formulations of drug, the two formulations can be incubated at room temperature or at an elevated temperature for an extended period of time (e.g., for several days at body temperature, 37° C.), then analyzed for drug content (by high performance liquid chromatography) and particle size distribution (by dynamic light scattering). The concentration of drug in formulations containing squalene remain essentially unchanged for longer periods of time than for solution formulations not containing squalene. Selection of other components for the squalene formulation, such as amphipathic excipients for squalene-water emulsions or for particles containing other polymers mixed with squalene (e.g., mixtures of PLGA and squalene) will be guided by the ability of the formulation to maintain colloidal dispersion and constant particle size over an extended period of time (e.g., one month at room temperature, 23-26° C.), as measured by dynamic light scattering.

Therapeutic Applications

Formulations described herein can be delivered by various methods to treat a variety of target tissues. In one embodiment an implanted drug delivery system is used and may include electrode(s) for stimulating tissues of the inner or middle ear. Alternatively, a catheter delivering drugs into the inner ear may be combined with an electrode array such as those used for restoring hearing. As another example, as described in Ser. No. 11/780,853, a terminal component can be a retinal (or other intraocular) implant providing electrical stimulation and delivering drug-containing vehicle. As other examples, electrical stimulation and drug delivery may be used to treat the tissues of the deep brain (e.g., a treatment of Parkinson's disease), spine (e.g., a pain management), or inferior colliculus or auditory cortex for tinnitus or hearing related diseases. Deep brain stimulation may be used in conjunction with drug delivery for treatment of chronic pain states that do not respond to less invasive treatments. In some implementations, electrodes may be implanted in the somatosensory thalamus or the periventricular gray region. In some cases, the drug delivery system and implanted electrical stimulator may be located in two separate locations in the body. For example, stroke rehabilitation patients who receive electrical stimulation in their extremities (e.g., forearm or legs) to restore motor function may also receive plasticity-enhancing drugs in the brain (e.g., motor cortex) via an implanted drug delivery system.

Drug delivery systems preferably include a pump, such as a valveless impedance pump, MEMS (Micro-Electro-Mechanical System) pump, osmotic pump, or piezodiaphragm pump. The drug delivery system preferably includes a rechargeable battery, a wireless remote control device, and a drug reservoir. The pump and reservoir preferably are fully implanted, and the fully implanted pump and reservoir with electronic components and battery communicates wirelessly with the remote control device, which is enabled for wireless communication and instructing the battery recharging or communicating with a dedicated wireless recharging system.

Depth and location of insertion of terminal components of such pumps depends on which region is being targeted. A cannula or needle may have an insertion stop which controls the depth of insertion. One preferred location for an incision in the eye is in the pars plana. One preferred location for terminating the cannula for drug delivery may be in the vitreous or the anterior chamber, allowing drugs to be delivered in controlled doses to the precise area of the eye. The terminal end of the catheter may be fixed, for example via suture, surgical tack, a tissue adhesive, or a combination thereof, to tissue near the outer surface of the eye. When attached, the catheter does not affect or otherwise restrict movement of the eye. Examples of devices and methods for ophthalmic drug delivery are disclosed in Ser. No. 11/780,853.

See also:

U.S. patent application Ser. No. 11/337,815 (published as Pub. No. 20060264897), filed Jan. 24, 2006, titled "Apparatus and Method for Delivering Therapeutic and/or Other Agents to the Inner Ear and to Other Tissues."

U.S. patent application Ser. No. 11/414,543 (published as Pub. No. 20070255237), filed May 1, 2006, titled "Apparatus and Method for Delivery of Therapeutic and Other Types of Agents."

U.S. patent application Ser. No. 11/759,387 (published as Pub. No. 20070287984), filed Jun. 7, 2007, titled "Flow-Induced Delivery from a Drug Mass."

U.S. patent application Ser. No. 11/780,853, filed Jun. 20, 2007, titled "Devices, Systems and Methods for Ophthalmic Drug Delivery."

U.S. Pat. No. 6,679,687, issued Jan. 20, 2004, titled "Hydro Elastic Pump Which Pumps Using Non-Rotary Bladeless and Valveless Operations."

U.S. Pat. No. 5,876,187, issued Mar. 2, 1999, titled "Micropumps with Fixed Valves."

U.S. patent application Ser. No. 11/850,156 (published as Pub. No. 20080065002), filed Sep. 5, 2007, titled "Catheter for Localized Drug Delivery and/or Electrical Stimulation."

U.S. patent application Ser. No. 11/831,230, filed Jul. 31, 2007, titled "Nanoparticle Drug Formulations."

U.S. Provisional Patent Application 61/022,224, filed Jan. 18, 2008, and titled "Implantable Drug Delivery Systems Having Valveless Impedance Pumps, and Methods of Using Same."

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Binding of Gacyclidine by PLGA Nanoparticles

Water (pH 7.2) was mixed with acetone solutions containing 2 grams/liter 5050 DLG 3E (PLGA, Lakeshore Biomaterials, solution A) or a solution of 2 grams/liter 5050 DLG 3E and 2 grams/liter gacyclidine base (solution B) or a solution of 2 grams/liter gacyclidine base (solution C). Rapid mixing was accomplished by pumping water into a T-mixer at 5 milliliters/minute and solution A, B, or C into the same T-mixer at 1 milliliter/minute. Analysis of the particles resulting from rapid mixing of water and solution A (PLGA nanoparticles) by dynamic light scattering determined they had an average diameter of 71 nanometers. Analysis of the particles resulting from rapid mixing of water and solution B (PLGA+gacyclidine) by dynamic light scattering determined they had an average diameter of 407 nanometers. Analysis of the particles resulting from rapid mixing of water and solution C (gacyclidine) by dynamic light scattering determined they had an average diameter of 473 nanometers. Reanalysis of the particles formed from solution B (PLGA+gacyclidine) after allowing the larger particles to settle at room temperature for either 24 hours or 3 days indicated that particles in the supernatant had an average diameter of 50 nanometers or 42 nanometers, respectively.

Acetone was eliminated from the suspension of particles prepared by mixing water with solution B by stirring the suspension in an open beaker for three days. The particle suspension was then passed through a 0.2 micrometer polyethersulfone syringe filter (VWR International) to eliminate larger particles. Following passage through the 0.2 micrometer filter, the particles in suspension had an average diameter of 55 nanometers. These nanoparticles were then concentrated by pressure dialysis with a 10,000 MWCO cellulose membrane (Amicon) to a final volume of 17 milliliters. The average particle diameter in the concentrated suspension was determined to be 53 nanometers by dynamic light scattering.

To determine the gacyclidine concentration in the nanoparticle suspension, an aliquot (20 to 50 microliters) was diluted with 10 millimolar hydrochloric acid to a final volume of 1.8 milliliter and then analyzed by high-performance liquid chromatography. Gacyclidine in the concentrated suspension was determined to be 0.68 millimolar (0.18 grams/liter; 3.1 milligrams gacyclidine base; 8% of the initial gacyclidine). When this suspension was passed through a 0.2 micrometer polyethersulfone syringe filter (VWR International) it further reduced the concentration of gacyclidine to 0.23 millimolar (0.06 grams/liter; 1.0 milligrams gacyclidine base; 2.5% of the initial gacyclidine). Adjusting the pH of the suspension to pH 9.1 by addition of 1 molar sodium hydroxide, resulted in precipitation of gacyclidine from solution. After filtration of the pH 9.1 nanoparticle suspension through a 0.2 micrometer polyethersulfone syringe filter (VWR International) the concentration of particles was not reduced, based on light scattering intensity, nor was the average diameter of particles (58 nanometers, post-filtration) substantially altered. However, the concentration of gacyclidine present in the nanoparticle suspension, after adjusting the pH to 9.1 and passage through a 0.2 micrometer filter, was reduced to approximately 0.02 millimolar (0.005 grams/liter; 0.09 milligrams gacyclidine base; 0.2% of the initial gacyclidine). Based on the final amount of gacyclidine remaining associated with the PLGA nanoparticles, gacyclidine does not have a high affinity for PLGA. Very little of the gacyclidine in the initial nanoparticle preparation was bound to the PLGA nanoparticles, but was instead dissolved in the aqueous phase surrounding the particles.

EXAMPLE 2

Preparation of Squalene Nanoparticle Emulsions

A suspension of squalene was prepared by suspending 4.3 milliliters of squalene, 0.5 milliliters of polysorbate 80, and 0.5 milliliters of sorbitan trioleate in water and bringing the suspensions to a final volume of 100 milliliters in a volumetric flask. The suspension of squalene in water was passed through a Microfluidics M-110S high pressure homogenizer equipped with a G10Z 87 micrometer ceramic interaction chamber at 23,000 pounds per square inch. After one passage through the high pressure homogenizer, the particle diameter of the squalene emulsion was determined to be 128 nanometers by use of a Horiba LB-550 dynamic light scattering particle size analyzer. After a second passage through the homogenizer, the particle diameter of the squalene emulsion was determined to be 136 nanometers by use of the particle size analyzer. The particle size of this emulsion remained constant in the range between 114 to 148 nanometers upon standing at room temperature for several days or following up to 11 additional passes through the homogenizer.

A suspension of squalene in Ringer's solution was prepared by suspending 4.3 milliliters of squalene, 0.5 milliliters of polysorbate 80, and 0.5 milliliters of sorbitan trioleate in water and bringing the suspension to a final volume of 100 milliliters with Ringer's solution in a volumetric flask. The suspension of squalene in Ringer's solution was passed through a Microfluidics M-110S high pressure homogenizer equipped with a G10Z 87 micrometer ceramic interaction chamber at 23,000 pounds per square inch. After 7 passes through the homogenizer at room temperature, the particle diameter of the squalene emulsion was determined to be 114 nanometers by use of a Horiba LB-550 dynamic light scattering particle size analyzer. After 7 additional passes of the emulsion through the homogenizer with the interaction chamber maintained in an ice bath, the average particle diameter was determined to be between 108 to 135 nanometers.

EXAMPLE 3

Stability of Squalene Nanoparticle Emulsions

The squalene emulsions in water or in Ringer's solution maintained colloidal dispersion over a period of three months at room temperature, as judged by visual inspection or analysis with the Horiba LB-550 dynamic light scattering particle size analyzer. These suspensions were subjected to high centrifugal force by placing 1 milliliter aliquots of either suspension in a plastic centrifuge tube and subjecting it to 15,000 revolutions per minute in a Hermle Z229 centrifuge. After 30 seconds of centrifugation at an average force of 30,000 times gravity (25,000 to 35,000×g) less than 15% of the bottom portion of the suspension had been cleared of nanoparticles. These results indicate that either formulation should maintain colloidal dispersion indefinitely, despite the somewhat lower density of the squalene nanoparticles than water.

EXAMPLE 4

Preparation of Gacyclidine-Containing Squalene Nanoparticle Emulsions

Squalene was added to 1 gram of gacyclidine free base in 1 milliliter aliquots until the gacyclidine base went into solution. The minimum amount of squalene required to dissolve 1 gram of gacyclidine base was 9 milliliters. A suspension of gacyclidine-containing squalene was prepared by adding 4.3 milliliters of the gacyclidine solution in squalene (1 gram gacyclidine base dissolved in 9 milliliters squalene), 0.5 milliliters of polysorbate 80, 0.5 milliliters of sorbitan trioleate, 35 milligrams of dipotassium phosphate, 1 milligram of citric acid, and 877 milligrams of sodium chloride to a graduated cylinder and bringing the mixture to a final volume of 100 milliliters with water. The suspension of squalene-gacyclidine in phosphate buffered saline was passed through a Microfluidics M-110S high pressure homogenizer equipped with a G10Z 87 micrometer ceramic interaction chamber at 23,000 pounds per square inch. After 7 passes through the homogenizer with the interaction chamber maintained in an ice bath, the average particle diameter of the squalene-gacyclidine emulsion was determined to be 135 nanometers by use of a Horiba LB-550 dynamic light scattering particle size analyzer. After 7 additional passes of the emulsion through the homogenizer with the interaction chamber maintained in an ice bath, the average particle diameter was determined to be 122 nanometers. After 7 additional passes of the emulsion through the homogenizer with the interaction chamber maintained in an ice bath, the average particle diameter was determined to be 114 nanometers. After 7 additional passes of the emulsion through the homogenizer with the interaction chamber maintained in an ice bath, the average particle diameter was determined to be 112 nanometers. Extensive analysis of the squalene-gacyclidine emulsion determined that the average particle diameter was between 107 to 123 nanometers. The pH and osmolality of the squalene-gacyclidine emulsion were determined to be 7.6 and 279 milliosmolal, respectively.

EXAMPLE 5

Stability of Squalene-Gacyclidine Nanoparticle Emulsions

The stability of the squalene-gacyclidine nanoparticle formulation was compared to a solution formulation containing 0.3 grams/liter of NST-001 hydrochloride salt dissolved in 10 millimolar aqueous hydrochloric acid. One 5 milliliter sample of the squalene-gacyclidine nanoparticle formulation was placed in a 5 milliliter acid-washed borosilicate glass pharmaceutical vial and sealed with a fluoropolymer-faced stopper. A second 5 milliliter sample consisting of 0.3 grams/liter of gacyclidine hydrochloride in 10 millimolar hydrochloric acid was placed in a 5 milliliter acid-washed borosilicate glass pharmaceutical vial and sealed with a fluoropolymer-faced stopper. Both vials were placed in an incubator that was maintained at 44±2° C. Periodically, samples were withdrawn from the 44° C. incubator; aliquots were taken for analysis by high-performance liquid chromatography; the vials were resealed; and placed back in the incubator. FIG. 1 shows the results of these analyses over a period of 32 days at 44° C. The solution formulation of gacyclidine hydrochloride decomposed with a rate of 0.115±0.001 day$^{-1}$ (time for 50% loss=6 days), while the squalene-gacyclidine nanoparticle formulation exhibits little or no loss of gacyclidine (rate<0.004±0.002 day$^{-1}$; time for 50% loss>170 days).

Figure 2:
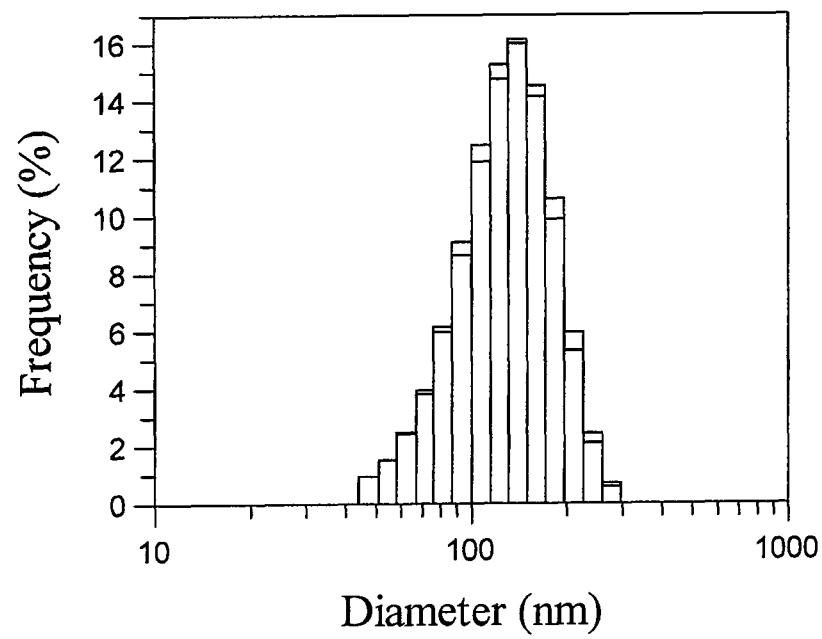
FIG. 2 shows the size distribution of gacyclidine-squalene nanoparticles immediately after preparation and after storage for one month at room temperature (23-26° C.), reflected by the slight change in the height of the bars representing the size of the nanoparticles.

The stability of the colloidal dispersion of squalene-gacyclidine nanoparticle formulation was further tested by comparing the size distribution of the formulation immediately after preparation with the same formulation after storage at room temperature for one month. FIG. 2 compares the size distribution of the formulation immediately after preparation and following one month of storage. Both profiles are nearly identical, with the average particle diameter ranging from 107 to 123 nanometers immediately after preparation and the average particle diameter ranging from 106 to 126 nanometers following one month of storage. Both static and dynamic light scattering intensities were also unchanged by one month of storage at room temperature, as judged by use of a Horiba LB-550 dynamic light scattering particle size analyzer.

EXAMPLE 6

Filtration of Squalene-Gacyclidine Nanoparticle Emulsions

Figure 3:
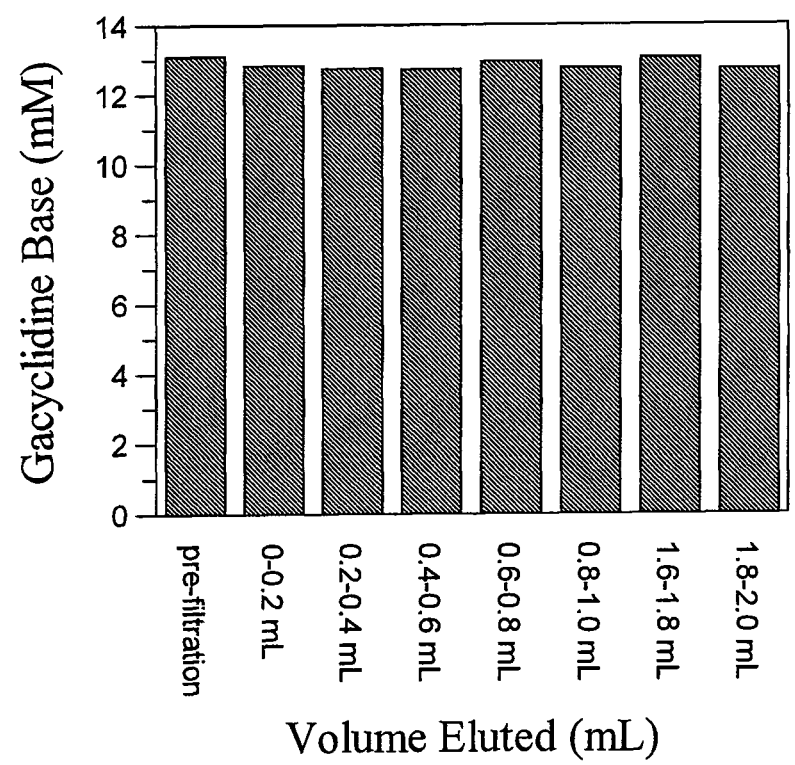
FIG. 3 shows the concentration of gacyclidine in a gacyclidine-squalene formulation before and after passage through a 0.2 µm antibacterial filter.

The ability of the squalene-gacyclidine nanoparticle formulation to pass through a filter was tested by filling a 3 milliliter BD Luer-Lok™ syringe with the formulation and manually expressing it through a sterile syringe filter equipped with a 0.2 micrometer polyethersulfone membrane filter (VWR Cat. No. 28145-501). The particle size and light scattering properties of the formulation were unchanged after passing through the filter. FIG. 3 shows the results obtained when 0.2 milliliter aliquots were collected from the formulation after passing through the antibacterial filter and analyzed for gacyclidine by high performance liquid chromatography. Based on these data, the concentration of gacyclidine in the squalene-gacyclidine formulation was not changed by passage through the antibacterial filter (FIG. 3).

EXAMPLE 7

Use of a Squalene-Gacyclidine Nanoparticle Emulsion in an Osmotic Pump

Figure 4:
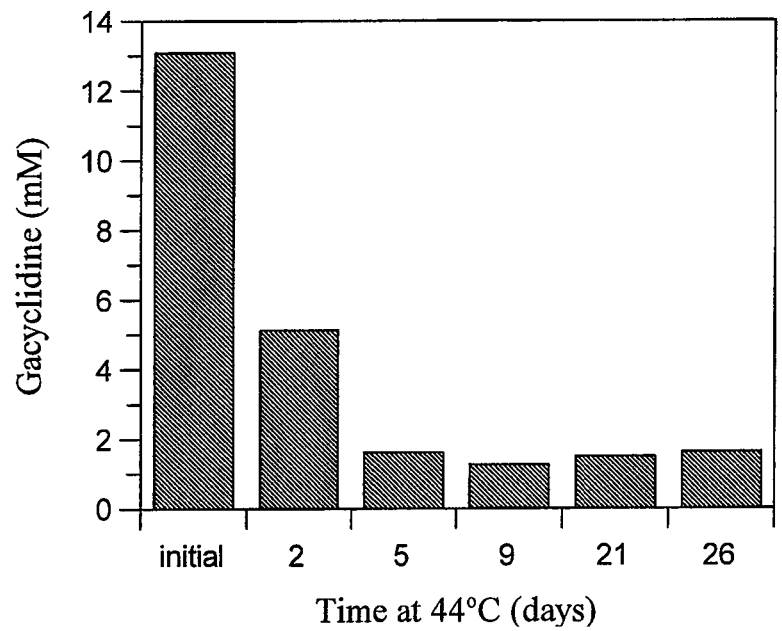
FIG. 4 shows the concentration of gacyclidine over time in samples of a gacyclidine-squalene formulation delivered by a mini-osmotic pump (model 2004, DURECT Corporation) at 44° C.

Delivery of gacyclidine from an osmotic pump containing the squalene-gacyclidine nanoparticle formulation was tested by delivering it from an ALZET® mini-osmotic pump, Model 2004, at 44° C. over a period of 26 days (FIG. 4). The osmotic pump was filled with a squalene-gacyclidine nanoparticle formulation prepared according to Example 4 and placed in a sealable container partially filled with Ringer's solution. Before placing the osmotic pump into the sealed container a collection tube with an internal diameter of 0.01 inches and consisting of polytetrafluoroethylene (PTFE) was attached to the pump to receive the formulation output by the action of the osmotic pump. The osmotic pump was submerged in Ringer's solution, and the pump containing the formulation, sealed container, and collection tube were placed in an incubator at 44° C. Periodically the formulation in the collection tube was transferred to an autosampler vial, and the gacyclidine concentration in the output from the osmotic pump measured by high performance liquid chromatography. After two days at 44° C., the gacyclidine concentration in the formulation delivered from the osmotic pump was 5.1 millimolar, which was 39% of the initial concentration of gacyclidine in the squalene-gacyclidine nanoparticle formulation used to fill the pump (13.1 millimolar). The osmotic pump output between 2 to 5 days incubation at 44° C. was 1.6 millimolar, which was 12% of the initial gacyclidine concentration. Between 2 to 26 days of incubation at 44° C. the concentration of gacyclidine in the osmotic pump output was relatively constant (FIG. 4). The average concentration of gacyclidine in the output of the osmotic pump after equilibrium had been established at 44° C. (days 2 to 26) was 1.5±0.2 millimolar (FIG. 4).

EXAMPLE 8

Partitioning of Gacyclidine Between PTFE and Squalene-Gacyclidine Nanoparticles

Figure 5:
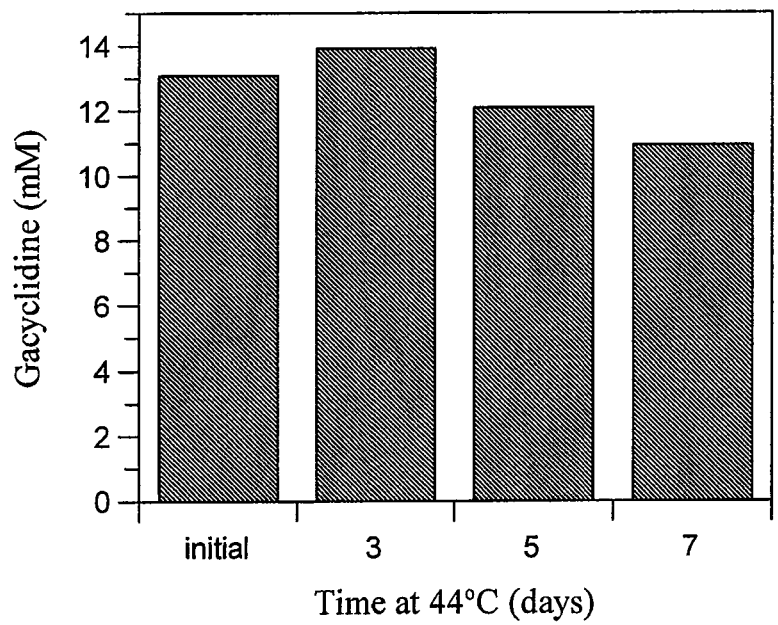
FIG. 5 shows the concentration of gacyclidine over time in samples of a gacyclidine-squalene formulation after incubation in polytetrafluoroethylene (PTFE) tubing at 44° C.

Partitioning of gacyclidine between fluoropolymer surfaces and squalene-gacyclidine nanoparticles was tested by filling 40 centimeters of PTFE tubing (internal diameter of 0.01 inches and an outer diameter of 0.02 inches) with 20 microliters of a squalene-gacyclidine nanoparticle formulation. After filling the PTFE tubing with the formulation, the ends of the tubing were joined with a short length of steel tubing (<4 millimeters). The tubing loops containing squalene-gacyclidine formulation were placed in a sealed container with Ringer's solution; and the container was placed in an incubator at 44° C. After 3, 5, or 7 days at 44° C., the squalene-gacyclidine formulation was analyzed for its gacyclidine content by high performance liquid chromatography (FIG. 5).

There was relatively little or no loss of gacyclidine from the squalene-gacyclidine formulation maintained at 44° C. in PTFE tubing (FIG. 5), in contrast to the losses encountered on delivery from the osmotic pump (EXAMPLE 7). At most there appears to be less than 21% loss of gacyclidine from the formulation, due to partitioning of drug between the squalene-gacyclidine nanoparticles and the internal surface of the PTFE tubing. The average recovery of gacyclidine was 92±14% (13.9 millimolar after 3 days; 106% recovery; 11.9 millimolar after 5 days; 91% recovery; and 10.3 millimolar after 7 days; 79% recovery). These results suggest that most of the loss of gacyclidine observed with the osmotic pump (about 89% loss at equilibrium) was due to binding of drug to the interior polymeric surface of the osmotic pump.

The invention claimed is:

1. A colloidal aqueous suspension, comprising nanoparticles that comprise squalene and a therapeutic agent selected from the group consisting of a phencyclidine analog, ifenprodil, traxoprodil, (±)-(R,S)-α-(4-hydroxyphenyl)-β-methyl-4-(phenylmethyl)-1-piperidine propanol, and carbamathione.

2. The colloidal suspension of claim 1, wherein the therapeutic agent is a phenycyclidine analog and the phenycyclidine analog is selected from the group consisting of gacyclidine and ketamine.

3. The colloidal suspension of claim 1, further comprising an amphipathic excipient.

* * * * *